United States Patent [19]

Bolanos et al.

[11] Patent Number: 5,423,858
[45] Date of Patent: Jun. 13, 1995

[54] SEPTOPLASTY FASTENERS AND DEVICE FOR APPLYING SAME

[75] Inventors: Henry Bolanos, East Norwalk; Dominick L. Mastri, Bridgeport, both of Conn.; Wayne P. Young, Brewster; Boris Zvenyatsky, Bronx, both of N.Y.

[73] Assignee: United States Surgical Corporation, Norwalk, Conn.

[21] Appl. No.: 129,910

[22] Filed: Sep. 30, 1993

[51] Int. Cl.⁶ ............................................. A61B 17/04
[52] U.S. Cl. ......................................... 606/220; 24/297; 24/453; 411/338; 411/517; 411/922
[58] Field of Search ............. 411/338, 354, 922, 517; 24/297, 453; 606/116, 117, 220, 151; 63/12

[56] References Cited

U.S. PATENT DOCUMENTS

| | | | |
|---|---|---|---|
| 2,367,657 | 1/1945 | Boersma | 24/453 |
| 3,238,835 | 3/1966 | Rosenberg | 411/338 |
| 3,251,260 | 5/1966 | Serdechny | 411/338 |
| 3,935,859 | 2/1976 | Doyle . | |
| 4,060,089 | 11/1977 | Noiles . | |
| 4,105,035 | 8/1978 | Rella . | |
| 4,236,385 | 12/1980 | Block | 63/12 |
| 4,353,370 | 10/1982 | Evans | 63/12 |
| 4,532,926 | 8/1985 | O'Holla | 606/220 |
| 4,592,357 | 6/1986 | Ersek . | |
| 4,669,473 | 6/1987 | Richards et al. | 606/220 |
| 4,694,781 | 9/1987 | Howe et al. | 606/117 |
| 4,759,670 | 7/1988 | Linder et al. | 24/453 |
| 4,932,960 | 6/1990 | Green et al. . | |
| 4,976,715 | 12/1990 | Bays et al. | 606/220 |
| 5,022,389 | 6/1991 | Brennan . | |
| 5,112,353 | 5/1992 | Johansson et al. . | |
| 5,135,342 | 8/1992 | Scott | 411/338 |
| 5,269,809 | 12/1993 | Hayhurst et al. | 606/232 |

FOREIGN PATENT DOCUMENTS

| | | | |
|---|---|---|---|
| 0116220 | 8/1984 | European Pat. Off. . | |
| 1309117 | 10/1962 | France | 411/338 |

OTHER PUBLICATIONS

Kern, E. B., Nasal Septal Reconstruction Versus Submucous Resection.

*Primary Examiner*—Gary Jackson

[57] ABSTRACT

A two-part fastener for use in septoplasty procedures includes a fastener portion having a base with shaft extending perpendicularly therefrom and a retainer having an aperture for engagement with the shaft. The fastener may include indexing means for positioning the retainer in engagement with the fastener portion at discrete spaced apart locations along the shaft. In another embodiment the shaft is slightly larger in diameter than the aperture in the retainer to effect a frictional engagement. Applicator instruments are also provided. In one embodiment the applicator includes two elongated members pivotally connected in the middle. In another embodiment the applicator includes an elongated body which holds a plurality of septoplasty fasteners. A pivotally connected lower jaw holds a supply of retainers. A pusher member drives the fastener through a curved firing chamber, through body tissue, and into engagement with the retainer.

9 Claims, 9 Drawing Sheets

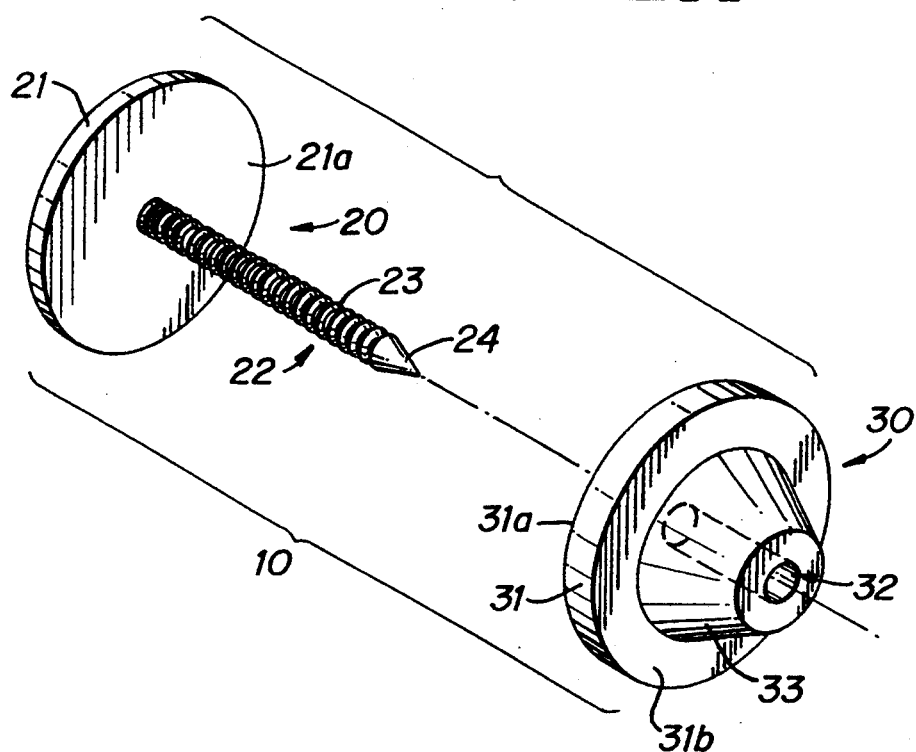
FIG_1
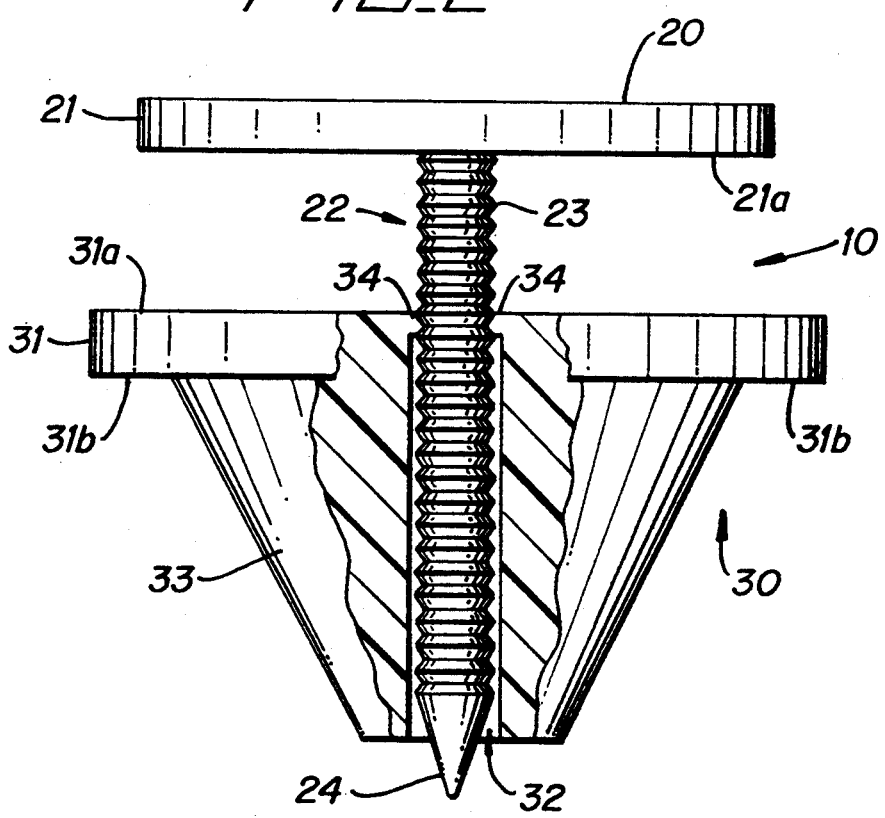
FIG_2

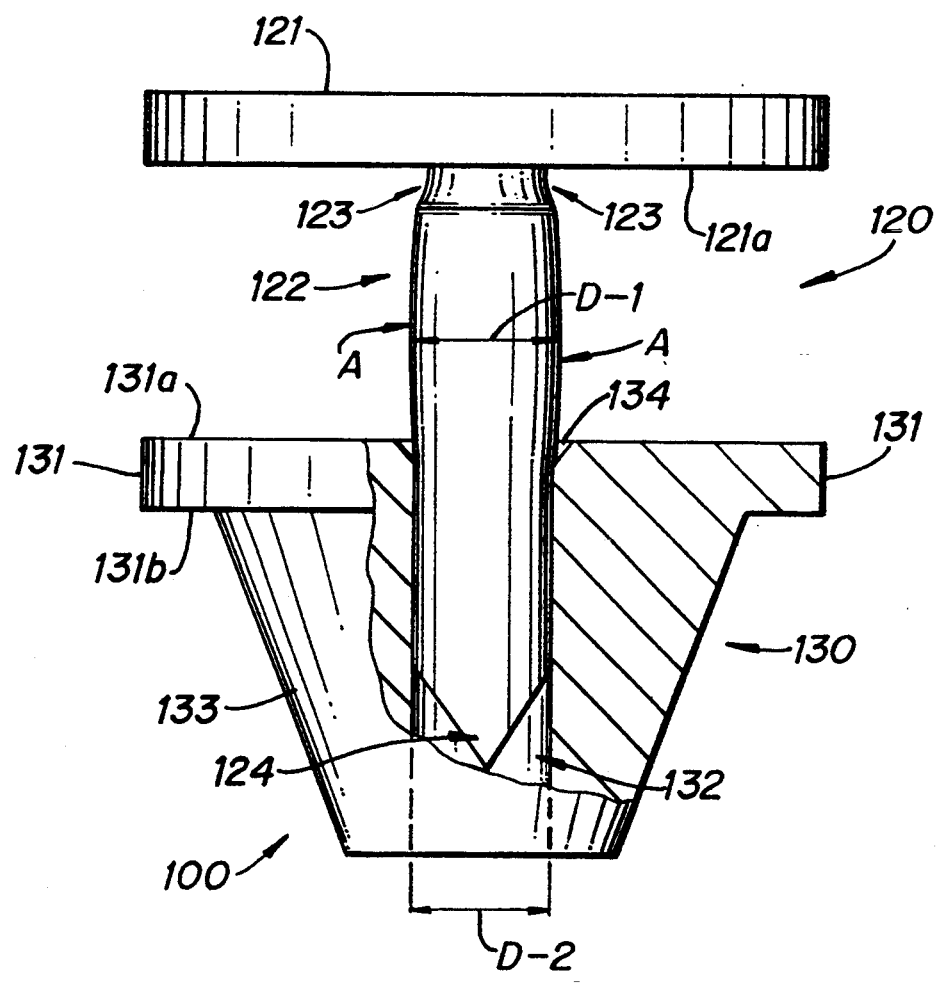
FIG_3

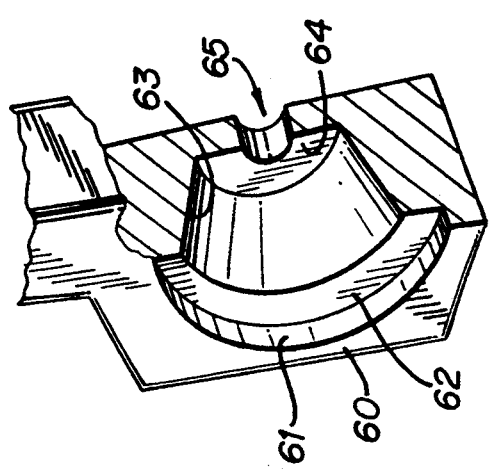
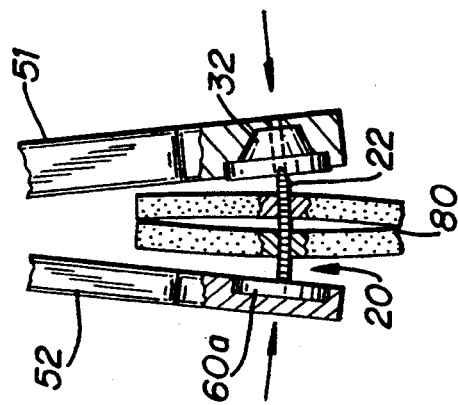
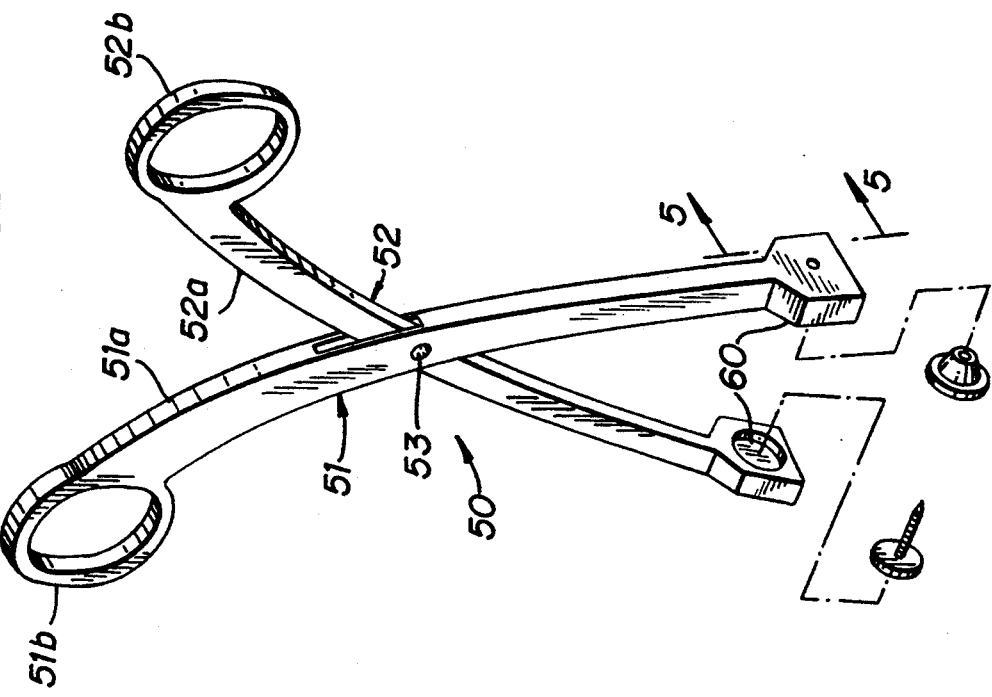

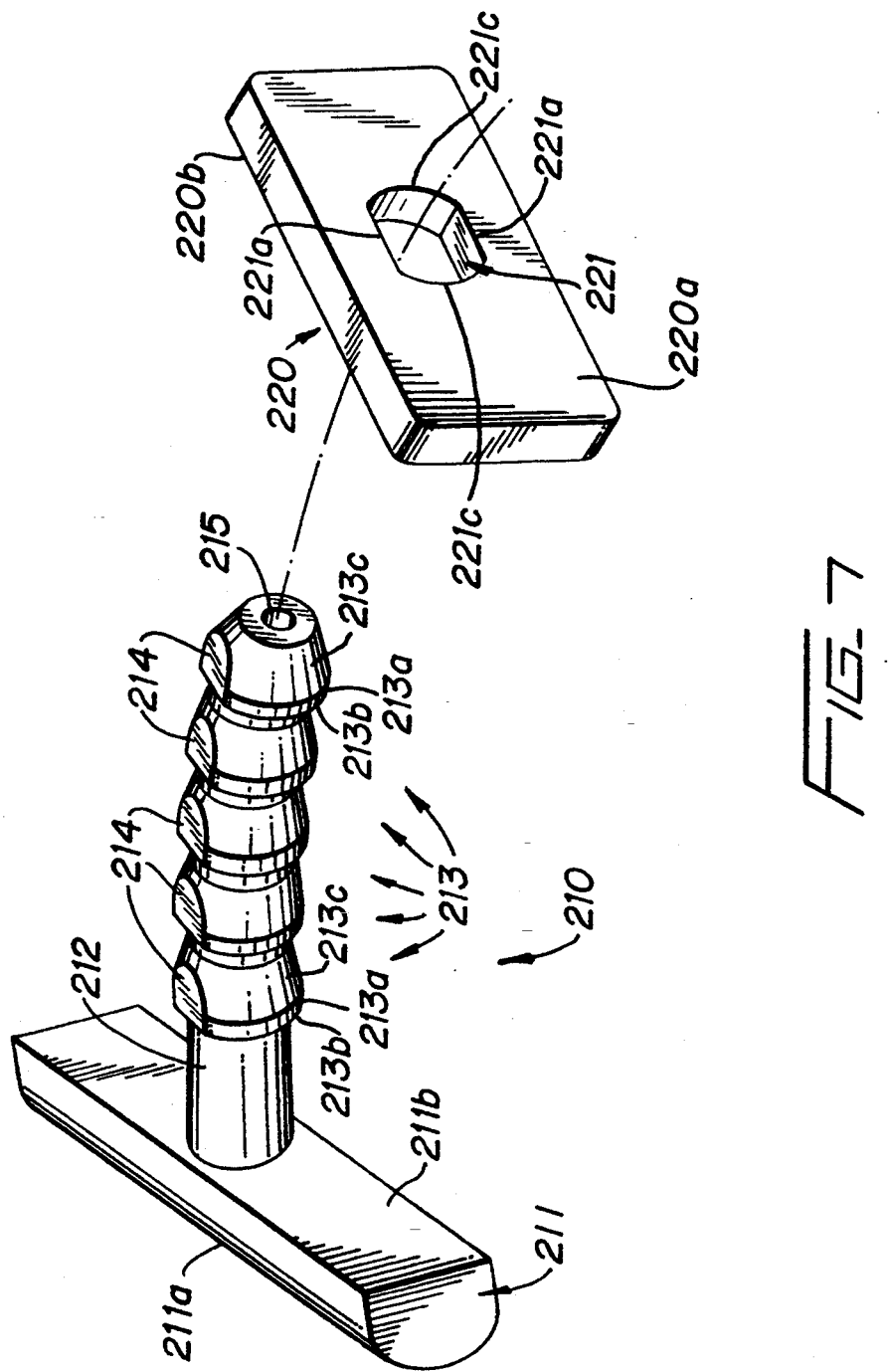

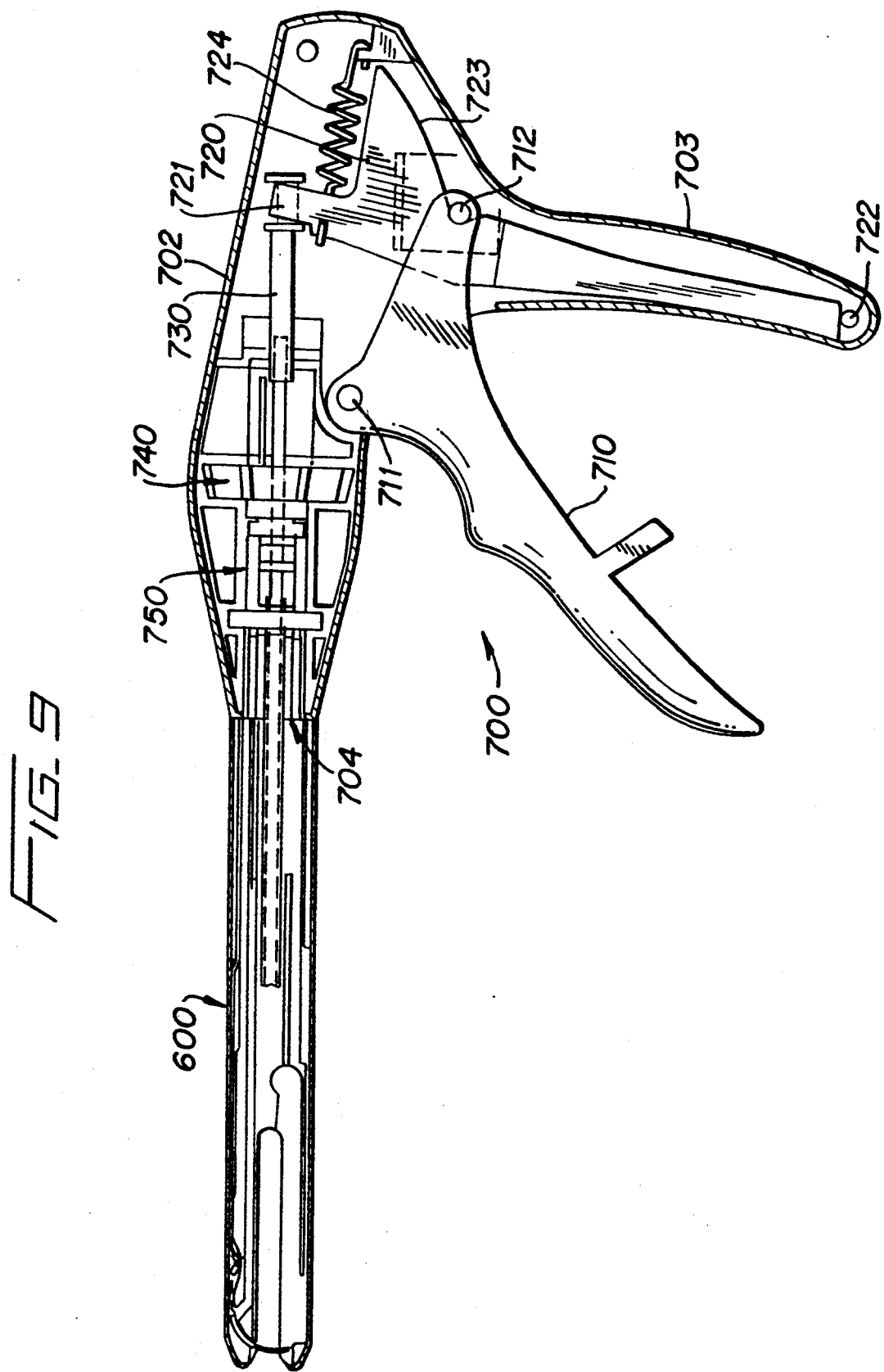

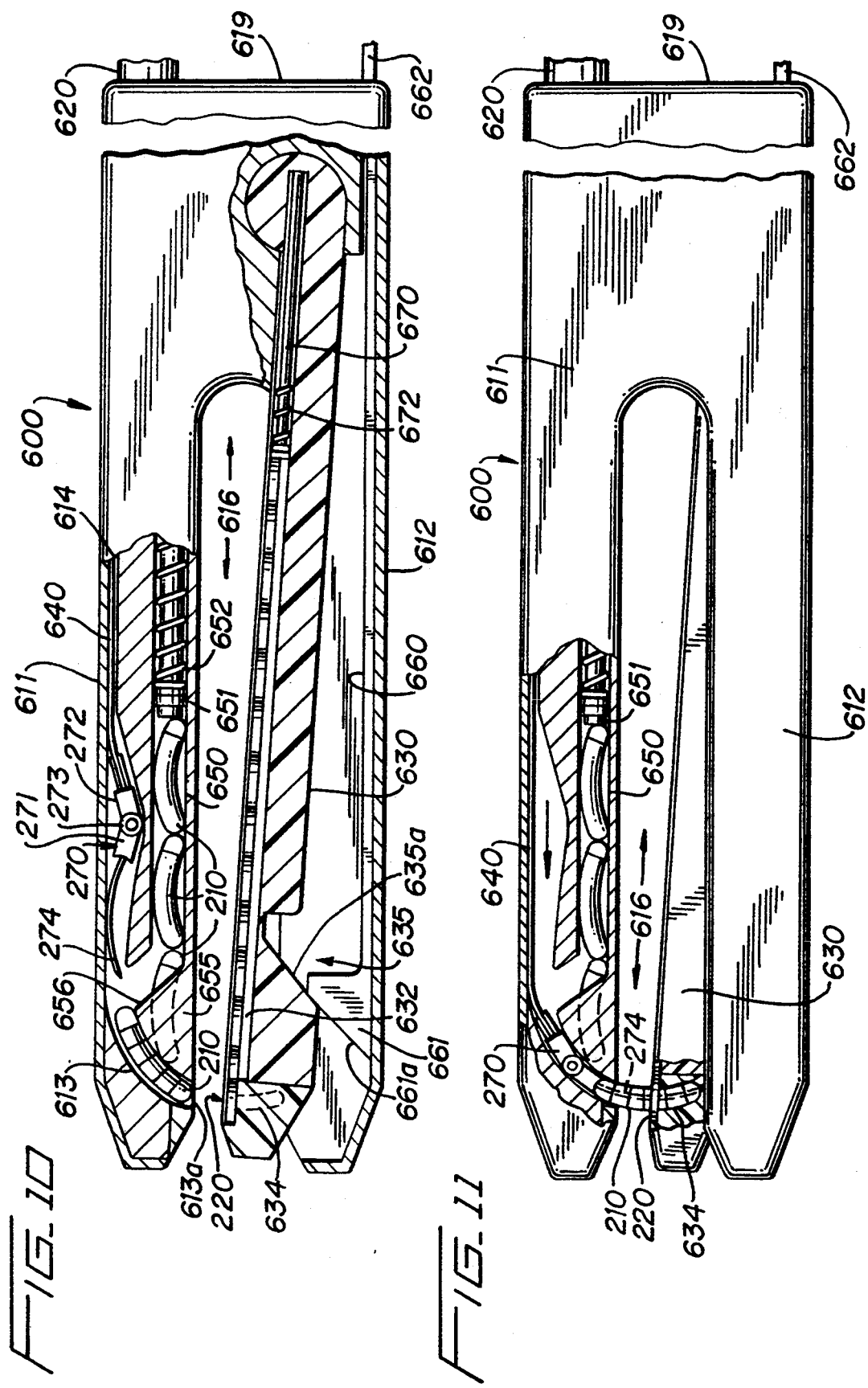

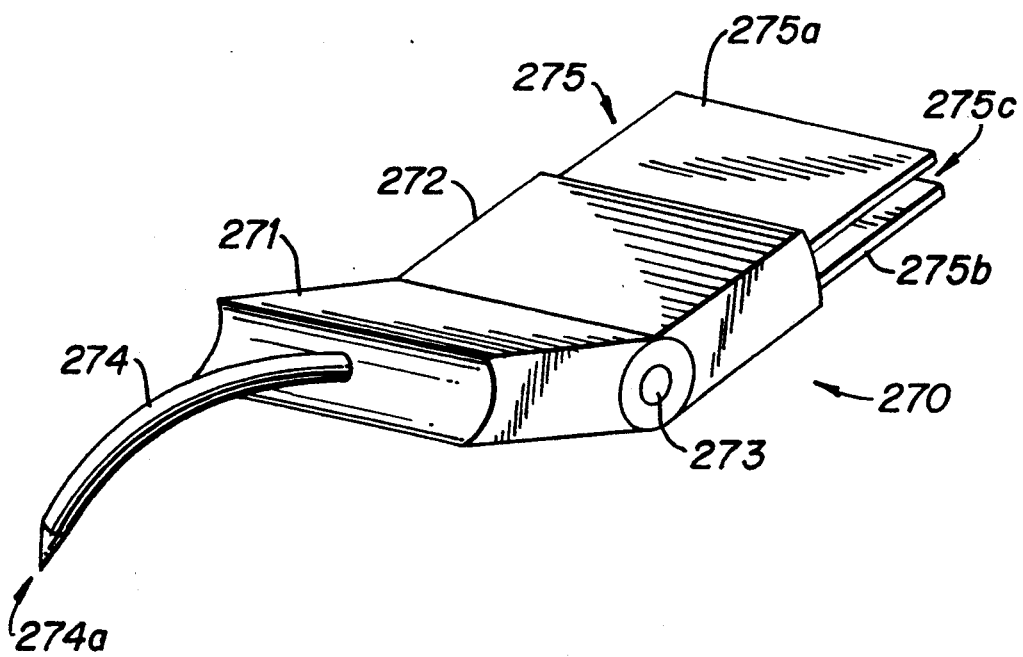
FIG_12

SEPTOPLASTY FASTENERS AND DEVICE FOR APPLYING SAME

BACKGROUND OF THE INVENTION

1. Field of the Invention

The present invention relates to surgical fasteners for use in septoplasty and to instruments for applying same.

2. Background of the Art

The septum is the cartilaginous wall which partitions the interior of the nose. The septum can be damaged by various agencies. Perforation of the septum is not uncommon and may result from, for example, physical injury and trauma, diseases, (e.g. syphilitic or tubercular ulceration), tumors, abscesses, and inhalation of corrosive chemicals and fumes.

Surgical reconstruction of the septum, i.e. septoplasty, often requires the support of the skin about the septum. In repairing a deviated septum, flaps of skin lining the nostrils on the sides of the septum are cut to expose the cartilage. Then excess cartilage is removed to open the airway through the nostrils. The flaps are then laid against the remaining cartilage and held in place for sufficient time for healing. One technique to hold the skin flaps in place is to stuff cotton into the nostrils. Another technique is to place a plastic sheet, such as polyethylene sheet cut out into the shape of the septum, on each of the two sides of the septum, and then pass transfixion stitches through the two support sheets and the septum to provide an external framework for the septum. This procedure can result in necrosis of the septum. Moreover, blood or mucus can accumulate under the plastic sheets and removal of the stitches can disrupt recently repaired tissue, especially if adhesions and/or encrustations have developed.

SUMMARY OF THE INVENTION

A two-part fastener for use in nasal constructive surgery is provided herein. In one embodiment the fastener comprises a fastener portion and a retainer portion. The fastener portion includes a first base having a distally facing first contacting surface, and a shaft projecting distally and substantially perpendicularly from the first contacting surface. Indexing means for positioning engagement of the retainer portion may be located at discrete spatial intervals along the shaft. The indexing means can comprise a series of spaced apart indentations located at predetermined intervals along the shaft. The retainer portion includes an axial bore for the reception of the shaft, the axial bore having a distal opening and a proximal opening.

This embodiment, as well as other embodiments of the fastener described herein, may be made from metal but is preferably fabricated from a bioabsorbable material such as polymers of glycolide, lactide, p-dioxanone, caprolactone, trimethylene carbonate, and physical and chemical combinations thereof.

In a second embodiment the fastener for use in nasal reconstructive surgery comprises a fastener portion and a retainer portion. The fastener portion includes a first base having a distally facing first contacting surface, and a shaft projecting distally and substantially perpendicularly from the first contacting surface. The retainer portion has an axial bore for the reception of the shaft. The axial bore has a distal opening and a proximal opening. The fastener portion and the retainer portion are fabricated from a resilient material, and the axial bore has an inner diameter slightly less than the widest outer diameter of the shaft. The proximal opening is preferably bevelled to facilitate entry of the shaft therethrough. The shaft has a tapered tip terminating in a tissue piercing point. Preferably the shaft has a reduced diameter portion in proximity to the junction between the shaft and the first base.

In a third embodiment the two-part fastener for use in nasal reconstructive surgery comprises a fastener portion and a retainer portion. The fastener portion includes a crosspiece having a distal surface and a proximal surface. The distal surface of the crosspiece is substantially flat, whereas the proximal surface of the crosspiece is preferably curved. A shaft extends distally and substantially perpendicularly from the distal surface. The shaft may be straight but is preferably curved in an unbiased state. The fastener portion has a fastener bore extending through the crosspiece and axially through the lengthwise extension of the shaft. The resilient and flexible retainer portion has an aperture for receiving the shaft. The shaft preferably has indexing means for positioning engagement of the fastener portion at discrete spatial intervals along the shaft. The indexing means comprises a plurality of spaced apart ridges, each ridge including an inclined distal surface and a proximal abutment surface, and wherein the aperture of the retainer has a diameter less than the cross sectional diameter of the shaft at the widest portion of the ridge, the retainer aperture resiliently deforming to permit passage of the shaft and ridges therethrough upon application of a force of suitable magnitude and direction to the fastener portion and/or retainer portion.

Also provided herein are applicator devices for the above mentioned fasteners. In one embodiment the applicator device comprises a pair of elongated members pivotally connected to each other and each having a handle portion and a fastener holding portion. The fastener holding portion of each member includes a fastener receiving aperture. The aperture includes a generally annular base support surface surrounded by a support wall, and a central aperture for permitting passage therethrough of the shaft.

An embodiment of an applicator device for applying a fastener of the third embodiment comprises an elongated body having a longitudinal axis, a distal end portion and a proximal end portion. The device has means for storing a plurality of surgical fasteners in a single file in a fastener storing chamber and means for advancing the distal-most fastener portion in the single file to a firing chamber. Drive means responsive to user applied force is provided to push the fastener portion from the firing chamber. A movable jaw is pivotally connected to the elongated body. The movable jaw and the distal end portion of the body define a gap for the reception therein of body tissue. Means associated with the movable jaw is provided for storing a plurality of retainer portions. Means associated with the movable jaw for advancing the distal-most retainer portion to a firing position is provided for receiving a fastener portion fired from the firing chamber.

The single file of fastener portions is oriented along the lengthwise extension of the elongated body. The means for advancing the distal-most fastener portion comprises a fastener advancing member which is distally biased by a spring connected thereto. The drive means comprises a user actuated plunger, a drive shaft connected to the plunger, and a fastener driver connected to the drive shaft.

The fastener driver comprises a driver body having a curved distal surface for contacting a proximal surface of a fastener portion, and a tissue piercing rod. The tissue piercing rod passes through the axial hole of the third fastener embodiment. The tissue piercing rod forms a hole in the septum cartilage for the fastener shaft to pass through. The firing chamber defines a curved path through which the fastener portion is moved when fired. The means associated with the movable jaw for advancing the distal-most retainer is spring biased. The advantage of using a curved fastener portion and curved driver is that it results in a slimmer instrument which is easier to maneuver in a nostril.

BRIEF DESCRIPTION OF THE DRAWINGS

FIG. 1 is an exploded perspective view of a two-part fastener of the present invention.

FIG. 2 is a partly cut-away elevational view of the two-part fastener of the present invention.

FIG. 3 is a partly sectional elevational view of an alternative embodiment of the two-part fastener.

FIG. 4 is a perspective view of an applicator for the two-part fastener.

FIG. 5 is a partly cut-away view of the distal end of the applicator.

FIG. 6 illustrates the application of the two-part fastener to body tissue.

FIG. 7 is an exploded perspective view of a third embodiment of the two-part fastener.

FIG. 9 illustrates an applicator instrument.

FIGS. 10 and 11 illustrate the distal end of the applicator instrument.

FIG. 12 is a perspective view of the pusher.

DETAILED DESCRIPTION OF PREFERRED EMBODIMENT(S)

Figure 7A:
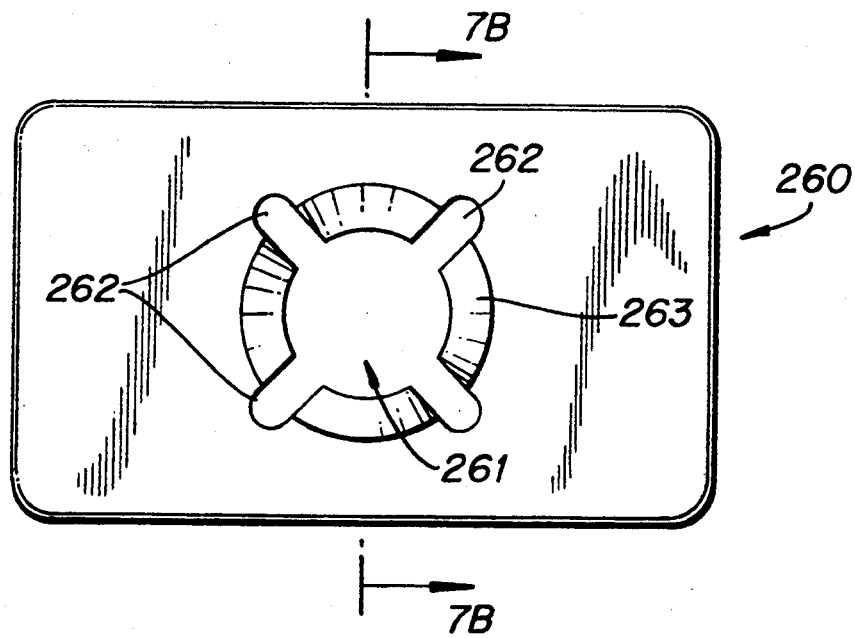
FIGS. 7A and 7B are plan and side views, respectively, of an alternative embodiment of the retainer portion.

Referring to FIGS. 1 and 2, the two-part septoplasty fastener 10 of the present invention comprises a fastener portion or tack 20 and a retainer portion 30.

The two-part fastener 10 may be fabricated from any suitable biocompatible material. Bioabsorbable materials are preferred, and each portion of the two-part fastener may be molded from such synthetic bioabsorbable material as polymers of lactide, glycolide, p-dioxanone, caprolactone, trimethylene carbonate, and chemical and physical combinations thereof. Fastener portion 20 comprises a planar and circular base 21 having a tissue contacting surface 21a, and a rectilinear shaft 22 projecting substantially perpendicularly from the center of the tissue contacting surface 21a. The shaft may optionally have serrations 23 extending circumferentially therearound. Also, the shaft 22 can have a relatively sharp pointed tissue piercing tip 24.

The retainer portion 30 includes a flat cylindrical base 31 having a tissue contacting surface 31a and an annular under surface 31b, a frustoconical portion 33, and an axial aperture 32 extending therethrough for receiving shaft portion 22 of the fastener portion 20, one end of aperture 32 providing an opening at the base, and the other end providing an opening at the lesser diameter end of the frustoconical portion 33.

At the mouth of aperture 32 opening at the base 31, an optional circular lip portion 34 extends radially inward. The lip portion 34 is configured and dimensioned so as to engage serrations 23. The lip 34 is, of course, resilient and flexes radially outward sufficiently to allow the peak of a serration to pass through the lip 34 then engages the next valley portion of the serration.

The engagement of lip 34 with the serrations 23 provides an indexing means since engagement of the retainer 30 relative to the fastener portion 20 can be positioned at any one of a multitude of discrete locations along the shaft.

An alternative embodiment of the fastener is shown in FIG. 3. Fastener 100 is a two-part bioabsorbable fastener comprising a fastener portion 120 and a retainer portion 130.

Fastener portion 120 comprises a planar circular base 121 having a tissue contacting surface 121a, and a rectilinear shaft 122 projecting perpendicularly from the center of the tissue contacting surface 121a. Shaft 122 has a relatively sharp point 124 for piercing tissue.

The retainer portion 130 includes a flat cylindrical base 131 having a tissue contacting surface 131a and an annular under surface 131b, a frustoconical portion 133, and an axial bore 132 extending therethrough for receiving shaft portion 122 of the fastener portion 120. One end of bore 132 provides an opening at the base 131, and the other end provides an opening at the lesser diameter end of the frustoconical portion 133. The mouth of bore 132 opening at the base 131 preferably has a bevel 134 to facilitate entry of shaft 122. The diameter of shaft 122 is at least equal to, and preferably slightly larger than, the diameter of the axial bore 132. Thus, insertion of shaft 122 into bore 132 requires the application of sufficient force. Once engaged, the shaft 122 is securely held in bore 132 by frictional contact between the walls and is not easily separated therefrom. The diameter D-2 of the bore 132 can be from about 90% to about 100% of the diameter D-1 of the shaft 122. Typically, the bore 132 diameter D-2 can be from about 0.040 inches to about 0.080 inches. The shaft 122 diameter D-1 can be from about 0.040 inches to about 0.090 inches.

To facilitate the insertion, fastener portion 120 is fabricated from a resilient composition of synthetic bioabsorbable polymer with sufficient rubberiness to allow the shaft 122 to be squeezed into the bore 132. A suitable composition comprises homopolymers and/or copolymers of glycolide, lactide, trimethylene carbonate, caprolactone, p-dioxanone, or blends of same. Typical polymer compositions are disclosed in U.S. Pat. Nos. 4,744,365 and 4,523,591, which are herein incorporated by reference. As the shaft 122 is squeezed in bore 132, the portion of the shaft outside the bore develops a shaft bulge A, as shown in FIG. 3. A circumferential reduced diameter portion 123 near base 121 permits room for expansion of the shaft as the bulge is moved along the shaft.

FIG. 4 shows a hand-held applicator 50 for fasteners 10 and 100. Applicator 50 comprises two tongs 51 and 52 pivotally mounted at point 53. The proximal end of the tongs have handles 51a and 52a, respectively, each having an aperture 51b and 52b, respectively, for the reception of the user's finger. The distal end of each tong has a fastener reception port 60 adapted to individually accommodate both the fastener portion 20 and the retainer 30. The reception ports face each other to accomplish engagement of the fastener portion 20 and retainer portion 30.

As shown in FIG. 5, each port 60 comprises a circumferential side wall 61 of such diameter to accommodate base 21 of the fastener portion, an annular surface 62 to support either the base 21 or the annular undersurface 31b of base 31, an inclined portion 63 to support the circumferential surface of frustoconical portion 33, and an annular surface 64 for supporting the annular end surface of the frustoconical portion. Aperture 65 permits passage therethrough of shaft 22.

In an alternative embodiment of the applicator, as shown in FIG. 6, one tong can have a reception port 60a adapted to receive only the fastener portion 20, the other tong can have a reception port 60, which is able to accommodate the retainer portion 30. Also, as shown in FIG. 6, to apply the fastener the fastener portion 20 and retainer 30 are each mounted in a respective one of the reception ports 60. The distal end of the applicator is positioned at the operating site with the tissue 80 to be fastened located between the distal ends of the tongs. The surgeon then presses the handle ends 51a and 52a, thereby bringing the distal ends together. The shaft 22 penetrates tissue 80 and engages aperture 32 of the retainer to a depth sufficient to secure the tissue. The tongs 51 and 52 may then be opened and withdrawn. The two-part fastener will remain in place due to the frictional engagement of the retainer 30 and fastener portion 20.

FIG. 7 illustrates an alternative embodiment of the present invention 200 comprising a fastener portion 210 and a retainer portion 220. The fastener portion 210 is a T-shaped member which comprises an elongated cross-bar 211 preferably having a convexly curved first surface 211a and a flat tissue contacting second surface 211b. A curved elongated shaft 212 projects perpendicularly from the tissue contacting second surface 211a at about the midpoint thereof. Shaft 212 includes a series of shaped ridges 213 along opposite sides of the shaft, each ridge projecting radially outward from the shaft and circumferentially extending partially therearound. Each ridge includes a first surface 213a, a second shop surface 213b, and a third surface 213c inclined relative to the shaft 212. A series of flat surface portions 214 are located on the shaft 212. This has the advantage of providing with a cross-section that does not rotate within retainer 220. However, other cross sections, e.g. rectangular, oval, or circular, may be employed. Optionally, the fastener portion 210 can be fabricated with a straight shaft to be accommodated by a straight firing chamber slot, as discussed below. Thus, the unbiased shaft can have an axial centerline which is rectilinear or which follows a curve C as shown by FIG. 8A and defined by a radius of from about 0.25 inches to about 0.40 inches.

The fastener portion 210 also includes an axial aperture 215 extending longitudinally through the fastener from the midpoint of the curved upper surface 211a to the distal end of shaft 212.

The retainer portion is a flat member 220 having a first surface 220a, a tissue contacting second surface 220b and an aperture 221. Aperture 221 is generally oval shaped and is bounded by straight edges 221a and curved edges 221c. Thus, aperture 221 is adapted to receive shaft 212 such that the straight edges 221a are oriented with the rows of flat surfaces 214, and the curved edges 221c are oriented with the ridges.

The length of long axis of the oval aperture 221 is slightly less than the cross sectional diameter of the shaft at the furthest extent of the ridge. As the retainer 220 and shaft 212 are pushed into engagement the curved edges 221c of the aperture 221 contact the inclined surface 213c of the first ridge. The resiliency and flexibility of the retainer allows aperture 221 to stretch sufficiently so that retainer 220 can be moved over the ridge 213. The fastener portion 210 and retainer portion 220 are preferably made from bioabsorbable polymer such as homopolymers and/or copolymers of glycolide, lactide, trimethylene carbonate, caprolactone, p-dioxanone, or blends of same. Typical polymer compositions are disclosed in U.S. Pat. Nos. 4,744,365 and 4,523,591. Most preferred are the annealed polymers of U.S. Pat. No. 4,744,365.

When the retainer has moved passed the first ridge into the space between the first and second ridges the retainer resumes its original shape and, since aperture 221 is of lesser diameter across its length than the diameter of the shaft at the ridge, any attempt to move the retainer back over the first ridge will be prevented by the abutment of surface 220a of the retainer against stop surface 213b of the first ridge. Thus, once engaged, the fastener portion 212 and retainer portion 220 cannot easily be separated.

The retainer may be further moved past the second, third, or fourth ridges depending on the thickness of the tissue layers to be fastened. The ridges, therefore, function as a convenient indexing means for indexing the position of the retainer 220 on the fastener shaft 212.

Figure 7B:
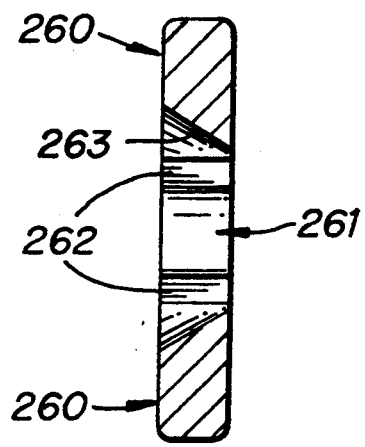

FIGS. 7A and 7B illustrate an alternative embodiment 260 of the retainer wherein retainer 260 includes a flat body having a central aperture 261. The edge 263 of the aperture is preferably bevelled to facilitate entry of a shaft. Moreover the aperture preferably also includes four elongated slots 262 oriented at approximately 45 degrees from the side edges of the retainer body. Retainer portion 260 is for use with a fastener shaft optionally having fins adapted to engage slots 262.

FIG. 9 illustrates an applicator portion 600 used in conjunction with a handle portion 700. Handle portion 700 includes a body 702 for housing the actuation mechanism, the body having a lower grip 703 and a nose portion with an opening 704 for receiving applicator 600.

A trigger 710 is pivotally mounted to the body at pivot pin 702 and includes a camming pin 712 on a proximal projection.

A pivot lever 720 is pivotally mounted to the lower portion of grip 703 at pivot pin 722 and includes a camming surface 723 which is cammed by camming pin 712. The pivot lever 720 has an upper projection 721 attached to the proximal end of a drive shaft 730. Drive shaft 730 is slidably mounted along the longitudinal axis of the apparatus and the linear motion of the drive shaft 730 along the longitudinal axis provides actuation means for operating applicator 600.

Rotation knob 740 is mounted to rotational coupling 750 which permits rotation of the applicator 600 while also permitting linear actuation motion of the drive shaft therethrough. Knob 740 extends outside an aperture in body 702 and is actuated by the user.

When trigger 710 is pulled by a user it pivots counter-clockwise (as shown). Camming pin 712 rides up surface 723 thereby pivoting pivot lever 720 also in a counter-clockwise direction. The upper projection 721 urges drive shaft 730 distally forward to accomplish actuation of the apparatus. Upon release of the trigger 710, it pivots clockwise to its initial position of FIG. 9.

Referring to FIGS. 10 and 11, applicator portion 600 of the embodiment of FIG. 9 is illustrated. Applicator portion 600 is capable of holding and sequentially firing a plurality of two-part fasteners. More particularly, applicator 600 includes an elongated body 610 having upper and lower distally pointing extensions 611 and 612, respectively, separated by gap 616.

A drive rod 620 is slidably mounted within a longitudinal aperture in the body. A thin, flexible strip 640 is fixedly mounted to the distal end of the plunger and extends through a narrow rectilinear opening 614 in the upper member 611. The distal end of strip 640 is fixedly mounted to a reception port of a pusher member 270.

Referring now to FIG. 12, pusher member 270 comprises a distal first body portion 211, a proximal second body portion 272 pivotally connected to the first body portion at hinge 273, a distally pointing shaft 274, terminating in sharp point 274 and a proximal reception port 275 composed of two flat distally pointing projections 275a and 275b separated by a gap 275c for the reception of strip 640.

Figure 8B:
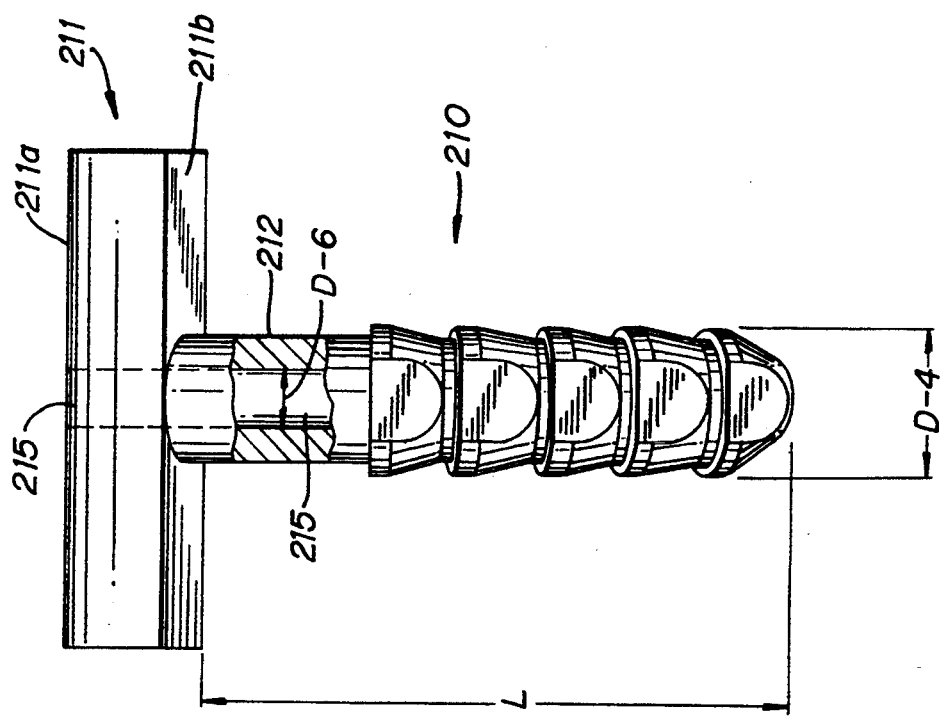
FIGS. 8A and 8B are side and elevational views, respectively, of the fastener portion.
Figure 8A:
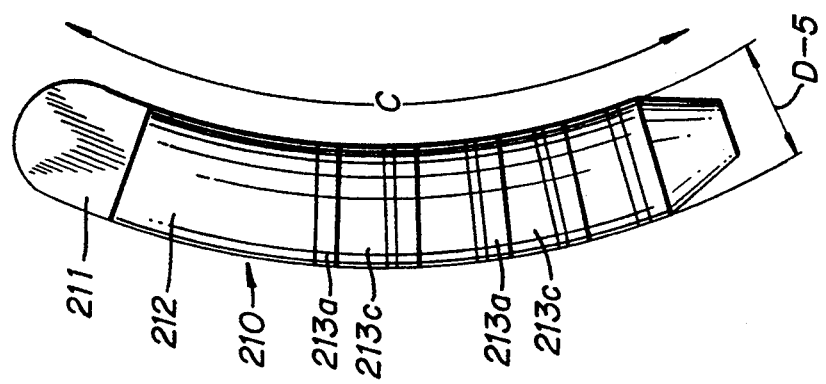

Referring once again to FIGS. 10 and 11 and also to FIGS. 8A and 8B, a plurality of curved fastener portions 210 are stored in a linear array in longitudinal chamber 650. An advancement rod 651 located behind the proximal-most fastener is distally biased by compression spring 652 to urge the line of fastener portions forward. The distal-most fastener is urged up a slotted ramp and into position in curved firing chamber slot 613. As can be seen, the fastener portions have curved shafts 212, the radius of curvature of the shaft 212 being substantially equal to the radius of curvature of the firing chamber slot 613. Generally, a radius of curvature of from about 0.25 inches to about 0.40 inches is preferred. Referring to FIGS. 8A and 8B, the length L of the shaft 212 typically ranges from about 0.20 inches to about 0.30 inches. The major outer shaft diameter D-4 ranges from about 0.040 inches to about 0.080 inches. The minor shaft diameter D-5 ranges from about 0.030 inches to about 0.070 inches. The shaft bore diameter D-6 ranges from about 0.020 inches to about 0.060 inches. Typically, D-6 is about 40% to about 85% of D-5. The shaft width ranges from about 0.10 inches to about 0.30 inches.

The ramp 655 comprises two spaced apart upward pointing planar projections separated by a central slot for passage therethrough of a fastener shaft 212. The projections each have a proximal sloped surface 656. When fastener portion 210 is urged forward the cross bar 211 rides up surface 256 and the fastener 210 is then urged into position in firing chamber 613, which has a lower opening 613a through which the fastener portion 210 exits when the applicator 600 is actuated.

A plurality of retainer portions 220 are mounted in a longitudinally oriented array on an upper shelf 632 of pivotally mounted retainer support arm 630 which is seated in lower extension 612. A slot 634 under aperture 221 of the retainer permits the fastener shaft 212 to pass through aperture 221 of the retainer. An advancement rod 670 located behind the proximal-most retainer portion is distally biased by compression spring 672 to urge the line of retainers forward.

The bottom of arm 630 includes a notch 635 with a distal camming surface 635a. Beneath arm 630 is a longitudinally slidable cam bar 660 with a distal portion 661 having camming surface 661a. Distal portion 661 is configured and dimensioned to be engaged with notch 635. The proximal end of support arm 630 is pivotally mounted. Consequently, when the cam bar is moved distally in response to user applied pressure applied to proximal end 662 of the cam bar, camming surface 661a cams against surface 635a of the arm, thereby moving the distal end of the arm 630 upward.

In use, the applicator 600 is positioned such that layer(s) of tissue to be fastened are located within gap 616. The camming bar 660 is pushed distally by pressure applied by the user to proximal end 662 of the cam bar, thereby bringing the retainer support arm 630 in contact with the body tissue. Drive rod 620 is then pushed distally by the user, thereby engaging the pusher 270 with the fastener portion 210 and pushing the fastener 210 out of the firing chamber 613, through the body tissue, and into engagement with the retainer 220. The drive rod 620 is pushed until the retainer is indexed to the desired position on the fastener shaft 212. The drive rod 620 and pusher 270 are then withdrawn and cam bar 660 moved proximally to release the tissue with fastener 200 now properly applied to the tissue.

While the above description contains many specifics, these specifics should not be construed as limitations on the scope of the invention, but merely as exemplifications or preferred embodiments thereof. Those skilled in the art will envision many other possible variations that are within the scope and spirit of the invention as defined by the claims appended hereto.

What is claimed is:

1. A fastener for use in nasal reconstructive surgery, which comprises:
   a) a fastener portion which includes a crosspiece having a distal surface and a proximal surface, a shaft integral with said cross-piece and extending distally from said distal surface, said shaft having a plurality of flat surface portions, said fastener portion having a bore extending through said crosspiece and axially through the lengthwise extension of said shaft;
   b) a resilient and flexible retainer portion having an aperture for receiving said shaft, said aperture being shaped so as to accommodate said flat surface portions of said shaft to prevent rotation of said fastener portion relative to said retainer portion when said fastener portion and retainer portion are mutually engaged; and
   c) indexing means on said fastener for positioning engagement of said fastener portion at discrete spatial intervals along said shaft.

2. The fastener of claim 1 wherein said fastener is fabricated from a bioabsorbable material.

3. The fastener of claim 2 wherein said bioabsorbable material comprises a synthetic polymer selected from the group consisting of polymers of glycolide, lactide, p-dioxanone, caprolactone, trimethylene carbonate, and physical and chemical combinations thereof.

4. The fastener of claim 1 wherein said distal surface of said crosspiece is substantially flat.

5. The fastener of claim 1 wherein said proximal surface of said crosspiece is curved.

6. The fastener of claim 1 wherein said indexing means comprises a plurality of spaced apart ridges, each ridge including an inclined distal surface and a proximal abutment surface, and wherein said aperture of said retainer has a diameter about 1% to about 20% less than the cross sectional diameter of the shaft at the widest portion of the ridge.

7. The fastener of claim 6 wherein said retainer aperture is resiliently deformable to permit passage therethrough of the shaft and ridges upon application of a force of suitable magnitude and direction to the fastener portion and/or retainer portion.

8. The fastener of claim 1 wherein said shaft has an axial centerline which is curved.

9. The fastener of claim 8 wherein the curvature of said axial centerline is defined by a radius of from about 0.25 inches to about 0.40 inches.

* * * * *